United States Patent
Ebels et al.

(10) Patent No.: US 10,413,400 B2
(45) Date of Patent: Sep. 17, 2019

(54) MECHANICAL HEART VALVE PROSTHESIS FOR THE RIGHT VENTRICLE

(71) Applicants: RIJKSUNIVERSITEIT GRONINGEN, Groningen (NL); ACADEMISCH ZIEKENHUIS GRONINGEN, Groningen (NL)

(72) Inventors: Tjark Ebels, Haren (NL); Hanna Pragt, Peize (NL)

(73) Assignees: RIJKSUNIVERSITEIT GRONINGEN, Groningen (NL); ACADEMISCH ZIEKENHUIS GRONINGEN, Groningen (NL)

( * ) Notice: Subject to any disclaimer, the term of this patent is extended or adjusted under 35 U.S.C. 154(b) by 0 days.

(21) Appl. No.: 15/553,072

(22) PCT Filed: Feb. 24, 2016

(86) PCT No.: PCT/NL2016/050133
§ 371 (c)(1),
(2) Date: Aug. 23, 2017

(87) PCT Pub. No.: WO2016/137321
PCT Pub. Date: Sep. 1, 2016

(65) Prior Publication Data
US 2018/0014929 A1 Jan. 18, 2018

(30) Foreign Application Priority Data
Feb. 24, 2015 (EP) ...................................... 15156392

(51) Int. Cl.
*A61F 2/24* (2006.01)
*F16K 15/03* (2006.01)

(52) U.S. Cl.
CPC .......... *A61F 2/2403* (2013.01); *A61F 2/2409* (2013.01); *A61F 2220/0091* (2013.01); *F16K 15/036* (2013.01)

(58) Field of Classification Search
CPC ..... A61F 2/2403; A61F 2/2406; A61F 2/2409
See application file for complete search history.

(56) References Cited

U.S. PATENT DOCUMENTS

| 4,373,216 A | 2/1983 | Klawitter |
| 4,808,180 A | 2/1989 | Johnson |
| (Continued) | | |

FOREIGN PATENT DOCUMENTS

| CA | 2105894 C | 8/2003 |
| EP | 0289404 A2 | 11/1988 |
| (Continued) | | |

OTHER PUBLICATIONS

Alemu, Y., et al.; "Design Optimization of a Mechanical Heart Valve for Reducing Valve Thrombogenicity—A Case Study with ATS Valve", Biomedical Engineering, ASAIO Journal, 2010, pp. 389-396.

(Continued)

*Primary Examiner* — Brian A Dukert
(74) *Attorney, Agent, or Firm* — Pearne & Gordon LLP

(57) ABSTRACT

A prosthetic heart valve having a pair of cooperating leaflets mounted in a valve body to alternate between an open position where the flow of blood in a downstream direction is permitted and a closed position where the flow of blood in the reverse direction is counteracted. Pivot member sets at diametrically opposite sides of each leaflet guide the leaflets moving between the open and closed positions, each set including an ear or a recess cooperating with an associated cavity or knob of an interior surface of the valve body. Each ear or recess bounds at least one leaflet passageway (Continued)

through that ear or recess and located spaced from upstream and downstream ends of the ear for allowing flow through that ear and the associated cavity, or through that recess, when the leaflets are in the closed positions.

21 Claims, 7 Drawing Sheets

(56) References Cited

U.S. PATENT DOCUMENTS

| | | |
|---|---|---|
| 4,888,010 A | 12/1989 | Bokros |
| 5,116,367 A * | 5/1992 | Hwang ............... A61F 2/2403 623/2.26 |
| 5,137,532 A | 8/1992 | Bokros et al. |
| 5,197,980 A | 3/1993 | Gorshkov et al. |
| 5,246,453 A | 9/1993 | Bokros et al. |
| 5,308,361 A | 5/1994 | Bokros et al. |
| 5,354,330 A | 10/1994 | Hanson et al. |
| 5,545,216 A | 8/1996 | Bokros et al. |
| 5,641,324 A | 6/1997 | Bokros et al. |
| 5,772,694 A | 6/1998 | Bokros et al. |
| 5,861,029 A | 1/1999 | Evdokimov et al. |
| 5,908,452 A | 6/1999 | Bokros et al. |
| 6,296,663 B1 | 10/2001 | Patke et al. |
| 6,395,025 B1 | 5/2002 | Fordenbacher et al. |

FOREIGN PATENT DOCUMENTS

| | | |
|---|---|---|
| EP | 0790043 A2 | 8/1997 |
| WO | 00/38597 A1 | 7/2000 |

OTHER PUBLICATIONS

Waterbolk, T.W., et al., "Pulmonary Valve Replacement with a Mechanical Prosthesis", European Journal of Cardio-Thoracic Surgery, vol. 30, 2006, pp. 28-34.

* cited by examiner

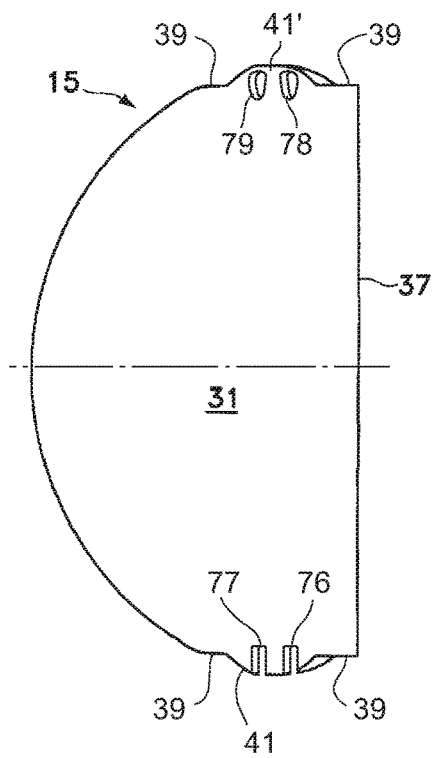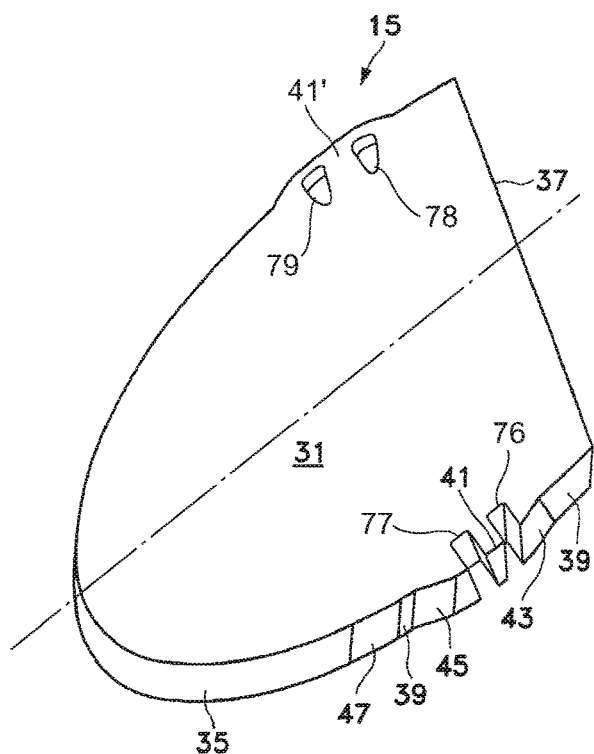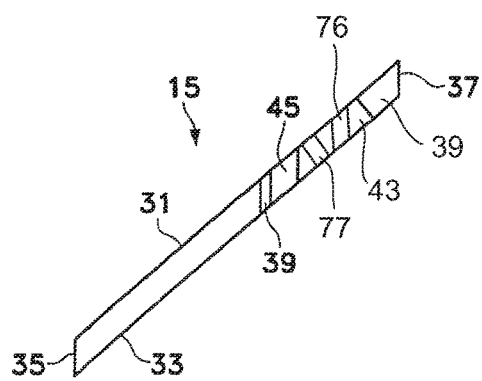

MECHANICAL HEART VALVE PROSTHESIS FOR THE RIGHT VENTRICLE

FIELD AND BACKGROUND OF THE INVENTION

The present invention relates to mechanical heart valve prostheses. Mechanical heart valve prostheses generally operate hemodynamically, in conjunction with the pumping action of the heart, to take the place of a defective natural valve. These valves have generally been designed to function with one or more occluders each swiveling to open and close a passageway through a generally annular valve body within which the occluders are suspended.

Pyrolytic carbon has been determined to be adequately non thrombogenic for use as a heart valve material. The problem of combatting thrombosis in mechanical valves is presently felt to lie in preventing excess turbulence, high shear stresses and local regions of stasis. Blood is a very delicate substance, and even minor abuses caused by turbulence and high shear stress can cause either thrombosis or emboli generation at local regions of stagnation. Regions of the valve that are particularly susceptible to the formation of thrombosis are the areas where the leaflets are pivotably suspended.

U.S. Pat. No. 5,861,029 discloses a mechanical heart valve having two projections at each side of each leaflet, one projection of each pair of projections being located above a rim in the valve body passageway and the other one of each pair of projections being located below the rim, so that the rim between the projections of each pair holds the pivotable leaflets in the valve body passageway. Slots in the valve leaflets leave open passageways to the outside of the pivoting area of the leaflets when the leaflets are closed.

U.S. Pat. No. 5,354,330 discloses a mechanical heart valve with a valve body having an interior wall surface with knobs cooperating with recesses in the side edge of said leaflet for keeping the leaflets in position, also during pivoting between the closed and open positions.

A valve with particularly low propensity of causing thrombosis is disclosed in U.S. Pat. No. 5,641,324 (embodiments of this valve have been approved by the U.S. Food and Drug Administration for usage with particularly low dosages of anticoagulants in the aortic position). The valve has a pivot arrangement with two pairs of diametrically opposed pivot member sets each formed by an ear projecting laterally from the side edges of the leaflet and a cavity in the interior surface of its valve body, each ear projecting into one of the cavities. The ears are shaped to allow some regurgitant flow around the ears when the leaflets are closed.

U.S. Pat. No. 6,296,663 discloses a mechanical bi-leaflet valve in which the leaflets each have ears projecting into mutually opposite recesses in the annular body. In this valve, the leaflets have notches allowing some regurgitant flow along the ears when the leaflets are closed.

These mechanical valves are specifically designed for implantation in the left ventricle. Maximum pressure drops (pressure differences between locations immediately upstream and downstream of the valve or occluders thereof) over the closed cardiac valve in the right ventricle are typically about eight times smaller than over the closed cardiac valve in the left ventricle. Accordingly, when a mechanical heart valve prosthesis is implanted in the right ventricle the flow through the valve hinges when the valve leaflets are in the closed position is much smaller than when the same valve would have been implanted in the left ventricle. This lower flow through the valve hinges is a probable cause for a higher incidence of clots originating from the valve hinge areas in mechanical heart valve prostheses in the right ventricle than in mechanical heart valve prostheses in the left ventricle. For this reason, mechanical prosthetic heart valves have not been popular for implantation in the right ventricle. However, the generally less thrombogenic alternatives of allograft (homograft) and biological heart valve prostheses have a much shorter lifetime than mechanical heart valve prostheses. This disadvantage is often exacerbated when the heart valve prosthesis is applied as a right ventricle heart valve prosthesis, because many diseases resulting in a need of a right ventricular heart valve prosthesis are innate diseases, so that patients receiving a first right ventricular heart valve prosthesis, often have a life expectancy that is a multiple of the lifetime of an implanted allograft (homograft) or biological heart valve prosthesis and therefore can expect to require multiple heart valve replacements, each involving heart surgery or delivery via a catheter and each preceded by a period of relatively poor performance of the heart valve prosthesis approaching its end of lifetime.

SUMMARY OF THE INVENTION

It is an object of the present invention to provide a mechanical heart valve prosthesis that is particularly suitable for use as a right ventricular heart valve prosthesis.

According to the invention, this object is achieved by providing a prosthetic heart valve including a generally annular valve body having an interior, generally arcuate wall surface which defines a valve body passageway for blood flow therethrough which is generally symmetrical about a longitudinal centerline, a pair of cooperating leaflets, the leaflets being mounted in the valve body to alternate between an open position where the flow of blood in a downstream direction is permitted and a closed position where the flow of blood in the reverse direction is counteracted, and a pivot arrangement with pivot member sets on diametrically opposite sides of each leaflet, which guides the leaflets in moving between the open and closed positions, the pivot member sets each comprising an ear projecting laterally from a side edge of the leaflet and a cavity in the interior surface of the valve body, the ear projecting into the cavity, or a recess in the side edge of the leaflet and a knob of the interior surface of the valve body, the knob projecting into the recess, each of the ear, ears, recess or recesses having opposite ends, the ends of each ear or recess being located upstream and downstream of that ear or recess when the leaflets are in the open position, and each of the ear, ears, recess or recesses bounding at least one leaflet passageway through that ear or recess, the at least one leaflet passageway being located spaced from the upstream and downstream ends of that ear or forming a leaflet passageway portion of the recess leaving a distance to the interior surface of the valve body, which is larger than a clearance between the interior surface of the valve body and portions of the side edge of the leaflet adjacent to the leaflet passageway, for allowing flow through that ear and the associated one of the cavities or through that recess when the leaflets are in the closed positions.

The leaflet passageways through the ear or, recess of each pivot member set allow flow through that ear and the associated cavity or through that recess when the leaflets are in the closed positions. Thus, a particularly effective flushing is concentrated in areas around the pivot axes of the leaflets, where the leaflets are suspended continuously and move relatively little as the leaflets move between open and closed positions, so the risk of formation of thrombosis would otherwise be relatively high. Moreover, this effect is of particular relevance at the low maximum pressure drops over a closed heart valve occurring in the right ventricle.

Particular elaborations and embodiments of the invention are set forth in the dependent claims. In a particular elaboration, the invention can also be embodied in a prosthetic heart valve including a generally annular valve body having an interior, generally arcuate wall surface which defines a valve body passageway for blood flow therethrough which is generally symmetrical about a longitudinal centerline, a pair of cooperating leaflets, said leaflets being mounted in said valve body to alternate between an open position where the flow of blood in a downstream direction is permitted and a closed position where the flow of blood in the reverse direction is counteracted, and a pivot arrangement which guides said leaflets in moving between said open and closed positions, said pivot arrangement comprising ears respectively projecting laterally from opposite side edges of each of said leaflets and two pairs of diametrically opposed cavities in said interior surface of said valve body, each of said ears projecting into an associated one of said cavities, said ears each having opposite ends, the ends of each ear being located upstream and downstream of that ear when said leaflets are in the open position, and each of said ears bounding at least one ear passageway through that ear, said at least one ear passageway being located spaced from said upstream and downstream ends of that ear for allowing flow through that ear and the associated one of said cavities when said leaflets are in said closed positions. Also such a prosthetic heart valve can be combined with the features of any of claims 2-12, 15 and 16.

Further features, effects and details of the invention appear from the detailed description and the drawings.

BRIEF DESCRIPTION OF THE DRAWINGS

FIG. 9 is a plan view of a leaflet, one half of which is of the first embodiment and the other half of which is of the second embodiment;

FIG. 10 is a perspective view of the leaflet embodiments of FIG. 9;

FIG. 11 is a side elevation view of the leaflet embodiments of FIGS. 9 and 10;

DETAILED DESCRIPTION

Figure 1:
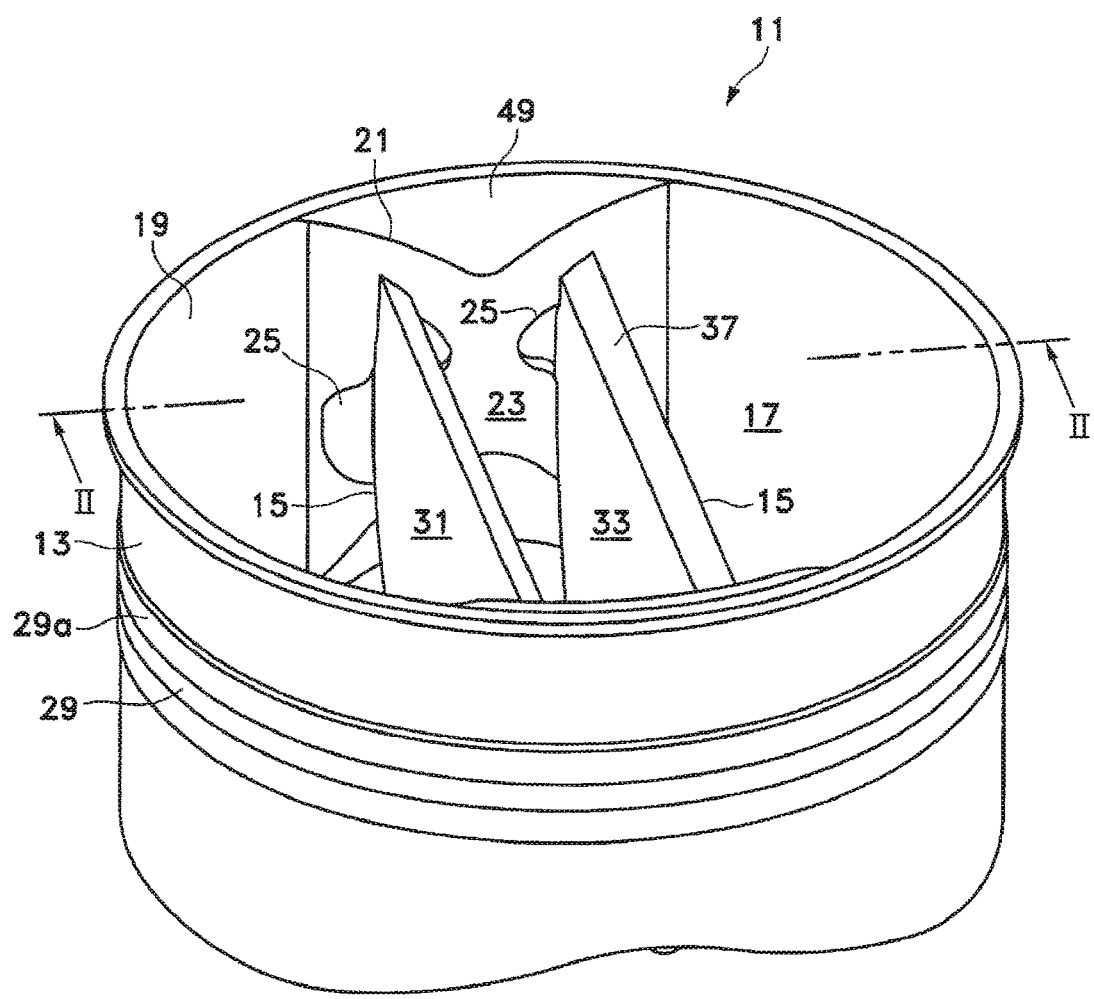
FIG. 1 is a perspective view of an example of a heart valve according to the present invention with leaflets in an open position.

FIGS. 1-12 show an example of a prosthetic heart valve 11 according to the present invention and a variant thereon, both examples being of a basic design as disclosed in U.S. Pat. No. 5,641,324, but with modifications. Heart valve 11 includes a generally annular valve body 13 which carries a pair of pivoting occluders or leaflets 15 that alternately open and close either to allow, when in open positions (FIGS. 1-3 and the left half of FIG. 8), the smooth flow of blood in the downstream direction, as indicated by the arrow A in FIG. 2, or to prevent, when in the closed positions (FIGS. 4, 5, and 12 and the right half of FIG. 8) substantial backflow of blood, i.e. regurgitation. The valve body 13 defines a valve body passageway bounded by its generally arcuate, mostly cylindrical interior wall surface 17. The valve body 13 has a curved entrance region 19 at its upstream end, which has been found to substantially increase streamlined flow characteristics through the valve with low turbulence and substantially no generation of thrombosis. A pair of diametrically opposed, thickened wall sections 21 protrude inward from an otherwise circular cylindrical surface, creating what is referred to as a tabulated cylindrical surface as a result of the thickened sections 21 terminating in facing, parallel flat wall surfaces 23 in which cavities 25 are formed that each function as one-half of a pivot member set which pivot member sets guide the opening and closing movements of the leaflets 15. Otherwise, the interior surface downstream of the curved entrance region 19 is generally rectilinear in axial direction of the passageway through the valve body 13.

The exterior surface of the valve body 13 in the region downstream of the flared entrance section 19 is substantially that of a surface of a right circular cylinder except for a slightly thickened central portion wherein a shallow groove 29 is formed between a pair of raised bands 29a. A metal stiffening attachment ring 30 with a plurality of circumferentially spaced apart inwardly protruding fingers 30a is mated therewith to add stability and rigidity to the valve body. The valve body is preferably made of a suitable material, such as pyrocarbon or pyrocarbon-coated graphite, as is well known in this art, which has sufficient resiliency that it can be deformed so as to permit the insertion of the pair of leaflets 15 in their operative locations. The metal ring 30 is also used to support the sewing ring of appropriate design, as broadly known in this art.

In the present example, the leaflets 15 are identical in shape and size. Each leaflet has two rectilinear, flat, surfaces forming an inflow surface 31 and an outflow surface 33. With the leaflets in the closed position (see FIG. 4), the inflow surface 31 faces upstream and the outflow surface 33 faces downstream. Although the leaflets 15 are flat, other configurations, such as sections of hollow cylinders of circular or elliptical cross section, can alternatively be employed, for instance as described in U.S. Pat. No. 5,246,453.

Figure 4:
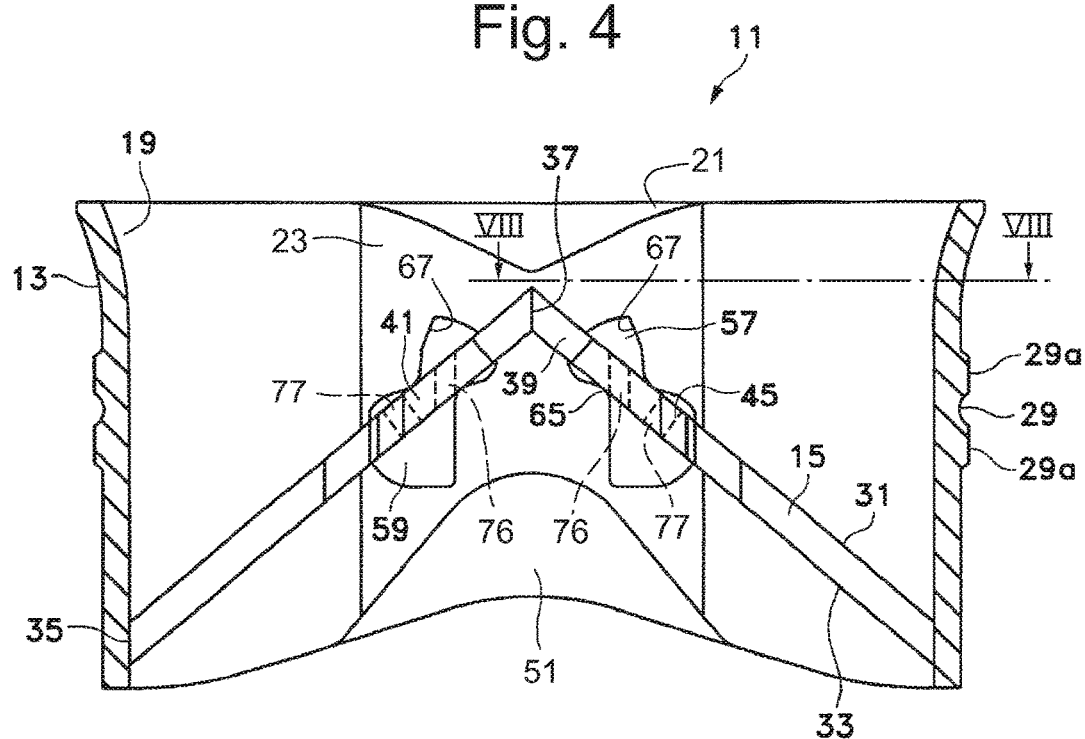
FIG. 4 is a view similar to FIG. 2, but with the leaflets in closed positions and the suture ring omitted.
Figure 5:
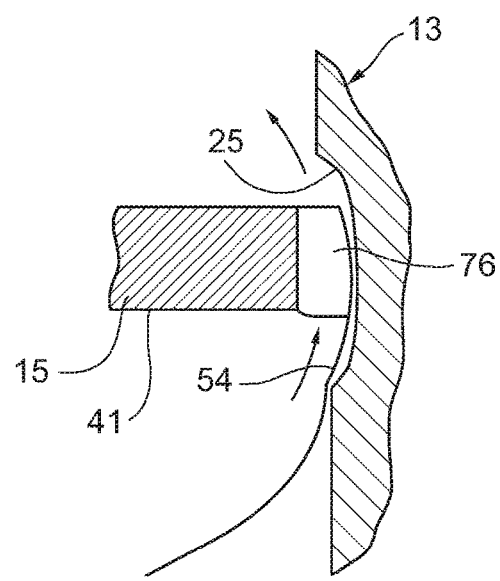
FIG. 5 is a fragmentary sectional view taken generally along line V-V of FIG. 8.
Figure 6:
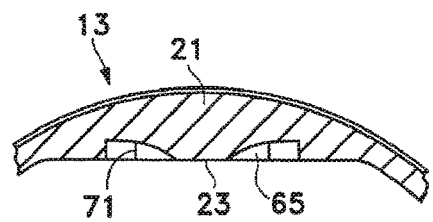
FIGS. 6 and 7 are fragmentary horizontal sectional views taken respectively along the lines VI-VI and VII-VII of FIG. 2, the leaflets being omitted.

The leaflets 15 each have a major arcuate edge surface 35, which is located at the downstream edge of the leaflet in the open position, and each has a minor mating edge surface 37 which is located at the opposite, upstream edge of the leaflet in the open position. The arcuate edge surface 35 abuts and shaped to seat closely against the cylindrical sidewall interior surface 17 of the valve body 13 when the leaflet 15 is in the closed position. The minor edge surface 37 is formed at an angle so as to mate flush against the corresponding mating edge surface 37 of the opposing leaflet when both leaflets 15 are in the closed position, as best seen in FIG. 4. The minor edge surface 37 is accordingly oriented at an angle to the inflow surface 31 which is substantially the same as the downstream angle which the outflow surface 33 forms with the centerline plane 64 (see FIG. 8) in the closed position, preferably an angle between about 30° and about 60°. The centerline plane 64 is defined as a plane which includes the centerline of the valve body passageway and which is parallel to the pivot axes of the leaflets. In the illustrated embodiment, the centerline plane 64 is perpendicular to the flat wall surfaces 23 of the valve body passageway. The angle the outflow and inflow surfaces form with the centerline plane 64 preferably corresponds to the extent of the angular rotation that each leaflet 15 undergoes when moving from the fully open position to the fully closed position or back.

As best seen in FIGS. 9-11, the leaflets 15 each have two pairs of intermediate straight edge regions 39 located between the minor mating edge surface 37 and the major arcuate edge surface 35, the straight edge regions 39 of each pair being located on opposite sides of a laterally extending ear or tab 41. As can be seen in FIGS. 10 and 11, the ears 41 are of the same thickness as the rest of the flat leaflets 15. The ears 41 are elongated in an upstream-downstream direction when viewed in their open orientation. The ears 41 have lateral edge surfaces, which are rectilinear surfaces of generally shallow curvature as viewed looking at the leaflet from the side of the inflow surface 31. More specifically, as best seen in FIGS. 10 and 11, they each have a shallow rounded upstream edge surface 43 and a generally similar downstream edge surface 45. The upstream edge surface 43 is the longer, extending generally laterally of the ear, and it meets and blends smoothly into the downstream surface 45. The major portion of the rectilinear upstream edge surface 43 is perpendicular to the flat inflow and outflow surfaces of the leaflets 15, which flat surfaces simply extend through the regions of the ears, so that the ears have inflow and outflow surfaces that are coplanar with the leaflet main body inflow and outflow surfaces 31, 33. A short arcuate transition edge section 47 is interposed between the major arcuate edge surface 35 and the flat section 39.

Figure 3:
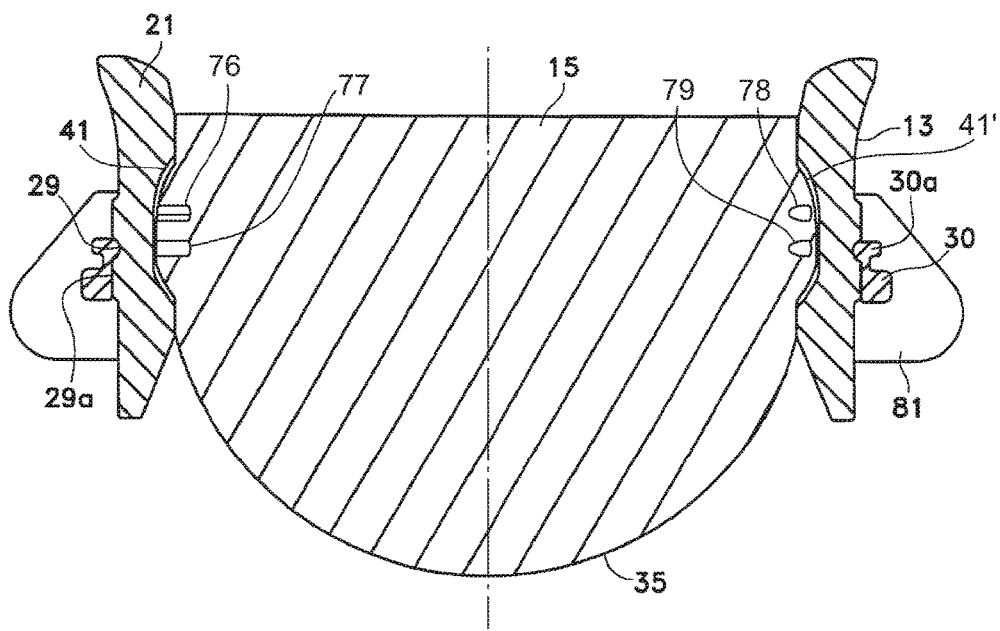
FIG. 3 is a vertical sectional view along line III-III of FIG. 2, one leaflet half being of a first embodiment and the other leaflet half being of a second embodiment.

As is best seen in FIGS. 3, 5 and 8-12, the ears 41 each bound two leaflet passageways 76, 77, in this embodiment designated as 'ear passageways' through that ear 41. In FIGS. 3, 9 and 10, one of the ears 41' is shown in the form of an alternative embodiment with ear passageways 78, 79 of a different design. Although not necessary, it is generally preferred that all the ears are of the same design. The ear passageways 76, 77, 78, 79 are each located spaced from the upstream and downstream ends of the respective ear 41, 41' for allowing flow through that ear and the associated cavity when the leaflets 15 are in the closed positions.

The thickened wall sections 21 of the valve body 13 in the regions where the cavities 25 are located are formed with an upstream transition surface 49 and a downstream transition surface 51 which lead smoothly from the circular entrance region and the circular exit region of the valve body 13 to the flat wall surfaces 23 wherein the cavities 25 are located.

Figure 8:
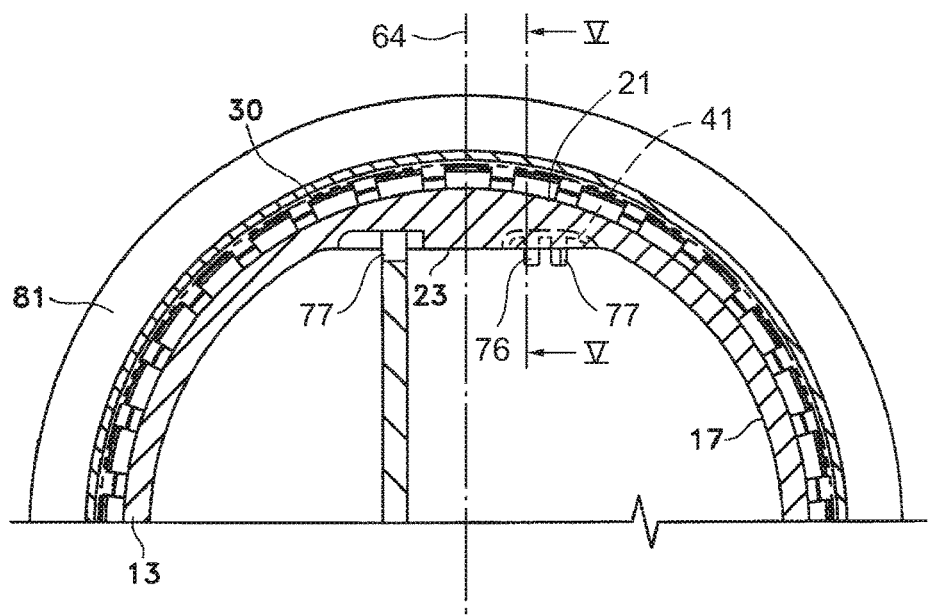
FIG. 8 is a combination of fragmentary sectional views taken along the lines VII-VII of FIG. 2 (left half of FIG. 8) and FIG. 4 (right half of FIG. 8)

Each thickened wall section 21 includes two side-by-side cavities which are mirror images of each other and which are located on opposite sides of the centerline plane 64. The depth of the cavities 25 is such that the apex of the curved upstream edge surface 43 of the ear does not quite touch the rear walls 54 of the cavities and a clearance of about 1-4 mils (0.001-0.004 inch) is left. The flat wall surfaces 23 of the thickened regions serve as the primary bearing surfaces against which the straight edge surfaces 39 of the leaflets bear. The clearance between the shallow curved edge surface 43 of the ear and the rear wall of the cavity allows some flow along the outside of the leaflet ears 41, 41' while the leaflets are closed (FIGS. 4 and 11 and left-hand portion of FIG. 8). This counteracts clotting in the pivot region. Because each of the ears 41, 41' of the leaflets 15 bounds at least one ear passageway 76, 77, 78, 79 through that ear 41, 41', the ear passageways 76, 77, 78, 79 being located spaced from the outer ends of the respective ear 41, 41', for allowing flow through that ear 41, 41' and the associated cavity 25 when the leaflets 15 are in the closed positions, a particularly effective flushing of the cavities 25 is achieved and ensured at the low maximum pressure drops over the closed heart valve occurring in the right ventricle. In the present example, the flows through the ears 41, 41' also entrains flow along the outside of the ears 41, 41', so that such flushing is also enhanced. Because the maximum pressure drop over the closed heart valve in the right ventricle is relatively low, the ear passageways 76, 77, 78, 79 through the ear 41, 41' do not result in excessively high regurgitant flow rates or velocities through the closed heart valve.

Figure 2:
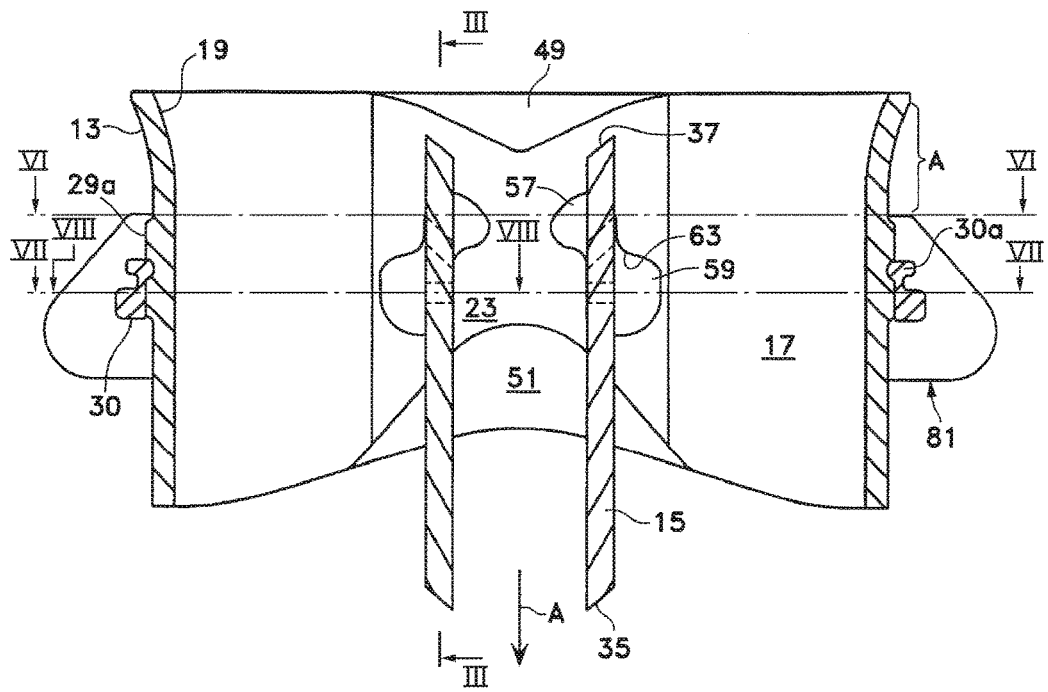
FIG. 2 is a sectional view along the line II-II of FIG. 1, but with a suture ring attached to the valve.
Figure 12:
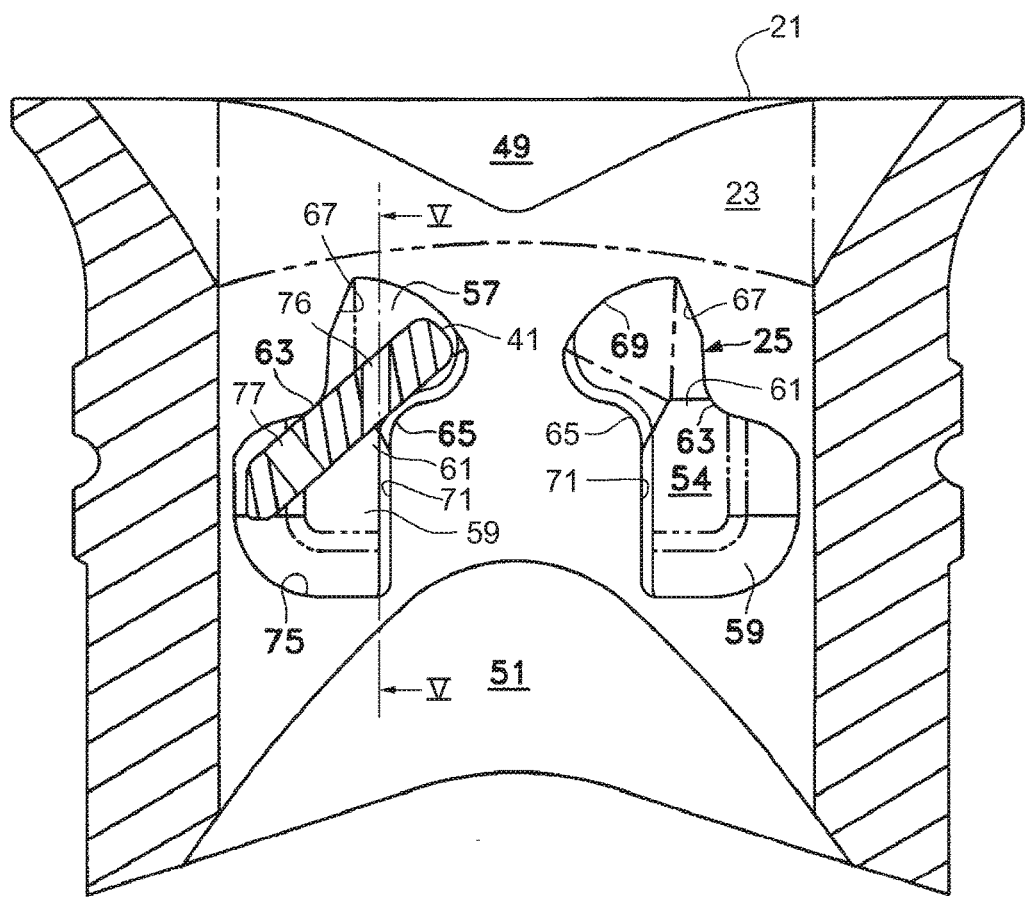
FIG. 12 is sectional side view through line XII-XII in FIG. 3, but with a right leaflet omitted and left leaflets in fully closed position.

As best seen in FIGS. 2, 4 and 12, the cavities 25 each have an upstream lobe 57 and a downstream lobe 59 on opposite sides of an intermediate throat section 61. The intermediate throat section 61 is bounded by a pair of curved fulcrums termed an outward fulcrum 63 and an inward fulcrum 65 with respect to their location having reference to the centerline plane 64. The outward fulcrum 63 is located substantially even with, but preferably slightly upstream of said inward fulcrum.

The upstream lobe 57 is formed with an inclined, straight, camming wall section 67, which is elongated in a direction oriented at an angle of between about 5° and about 30°, preferably between about 15° and about 25°, to the centerline plane 64.

The downstream lobe 59 includes a straight locator wall section 71 immediately below the inward fulcrum leading to the downstream end 75 of the cavity (FIG. 12). The flat wall section 71 is oriented parallel to the centerline plane 64 and thus provides a guide surface against which the outflow surfaces of the ears 41 bear in the full open position, as best seen in FIG. 2. As best seen in FIG. 11, the leaflet ears 41 preferably have their rounded downstream edge surfaces 45 oriented so as to be at an acute angle to the outflow surface 33 of the leaflet, thus presenting essentially a line of contact between the ear downstream edge surface 45 and the straight locator wall section 71, which tends to reduce friction and promote cleansing in this region.

The leaflets 15 are installed in the valve body 13 by squeezing the body at diametrically opposite locations, as for example along a diameter which is perpendicular to the centerline plane 64. Squeezing causes the diametrically opposed flat wall sections 23 to separate farther from each other, permitting the ears 41 to be passed into the cavities 25. When the squeezing force is removed, the valve body 13 returns to its original annular configuration, leaving only the desired minimal clearance between the flat wall surfaces 23 of the valve body and the straight lateral edge surfaces 39 of the leaflets, in which positions the leaflets are slidably-pivotally mounted for travel between the open and closed positions. The metal stabilizing ring 30 can be installed by snapping into place or by shrink-fitting, in the exterior circumferential groove 29 following the installation of the leaflets or before installing the leaflets.

Figure 7:
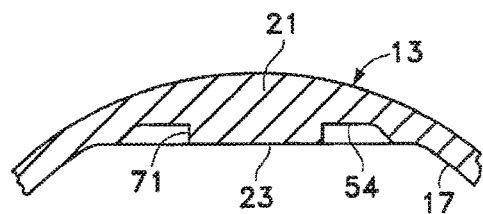

With the heart valve operatively installed in a patient, when it is in the open position, the two leaflets 15 assume an open equilibrium position with respect to the high flow and the direction of blood downstream through the passageway, which may be an orientation where they are substantially parallel to the centerline plane 64, as illustrated in FIGS. 1, 2 and the left half of FIG. 8. Should the dynamic blood forces within the valve body passageway change, the left or right hand leaflet can rotate slightly in closing sense so as to maintain such a low energy position either with or without some slight translation. In such an equilibrium position, the leaflets 15 provide very low obstruction to the downstream flow of blood. Yet, despite even such a substantially parallel, full open position, the pivot construction is such that any translational movement either downstream or upstream from this substantially parallel position causes the leaflets to rotate in the direction of closing. Furthermore, in the fully open position as shown in FIG. 2, the leaflets 15 are mounted so as to divide the valve body passageway into 3 sections, a center section located between the two leaflets 15 and two flanking sections. As best seen in FIG. 7, the arrangement is such that the cross-sectional area of each of the two flanking passageway sections is preferably at least as large as the cross-sectional area of the center flow passageway section.

During conditions of high rate of flow of blood downstream through the valve body, both leaflets 15 can be oriented substantially parallel to the centerline of the valve with the outflow surfaces of the ears 41 in contact with the flat wall sections 71 of the downstream lobes of the cavities 25 and with the ear upstream edge in juxtaposition with the camming wall 67 so that rotation past the parallel orientation is prohibited. The flow rate of blood through the valve during the pumping stroke of the associated chamber of the heart will generally exert sufficient force upon the inflow surfaces 31 of the leaflets such as to maintain the leaflets in this substantially parallel alignment. As the reverse flow of blood upstream through the valve begins, the leaflets 15 and the ears 41 immediately translate upstream. This upstream translation of the ears causes immediate camming engagement of the inflow surface edge of each upstream edge surface 43 against the adjacent straight camming wall section 67 of each cavity, while the outflow surfaces of the ears may slide along the rounded inward fulcrums 65. By camming engagement is meant contact wherein there is relative sliding movement along a surface which is inclined to the direction in which the net forces are attempting to move an object, i.e. upstream and parallel to the centerline of the valve body. This camming action causes the leaflet to very promptly pivot or swing toward its closed position while the translation movement continues until the upstream edges of the leaflet ears reach the top of the upstream lobes 57. Such initial pivoting is guided by the movement of the inflow surface edge of the ear upstream surface 43 along the camming surface 67 while the outflow ear surface generally slides along the inward fulcrum 65.

When the force of the backflowing blood against the outflow surface 33 of each leaflet has become significant, it causes the inflow surfaces of the ears to contact the outward fulcrums 63, and pivoting thereafter continues guided in part by sliding contact with the outward fulcrum 63. The leaflet has thus pivoted a significant amount as a result of the upstream translation and the shifting to contact with the outward fulcrum 63. Thereafter, the upstream edge surfaces of the ears are guided by movement along the arcuate wall section 69 while the ears simultaneously engage the outward fulcrums 63. Contact with the concave wall sections 69 and the fulcrums 63 remains substantially continuous for about the final one-half of the angular rotation of the ears, and the curvature of the wall 69 is designed so that substantially only rotational motion occurs as the upstream edge surfaces 43 slide therealong as the leaflets thereafter swing to the fully-closed position, illustrated in FIGS. 4, 5, the right hand half of FIG. 8 and FIG. 12. In such position, mating edge surfaces 37 of the leaflets abut each other, and the downstream arcuate edge surfaces 35 of the leaflets abut and seat against the cylindrical interior surface 17 of the valve body. During a major portion of the closing movement and specifically during the final stages, this motion is almost pure rotational motion to avoid sliding of the ears along the fulcrums at this time when the upstream edges of the ears move slightly downstream as a result of this rotation. When the mating edges 37 of the two leaflets meet, the contact between the upstream edge of each ear and the arcuate wall 69 is broken, as seen in FIG. 12, thus avoiding the possibility of localized wear when the pressure across the valve is highest. When the leaflet reaches its nearly closed position, the liquid between the edge 35 of the leaflet and the orifice wall acts like a cushion, and the leaflet further decelerates just before it impacts the wall, reducing the noise and any propensity for cavitation.

In the fully closed valve, with the leaflets 15 oriented as illustrated in FIG. 4, wherein they are shown in elevation, the force of the blood against the outflow surface 33 of each leaflet is borne mainly by the downstream arcuate edge surfaces 35 seating against the interior valve body surface and by the ears 41 bearing against the outward fulcrums 63. At the instant complete closure is achieved, the pressure of the blood against the outflow surfaces of the leaflets is at its highest and results in regurgitant flow through the ear passageways 76, 77, 78, 79. This causes effective flushing of the central areas of the cavities 25 that are most susceptible to the formation of thrombosis due to stagnation of blood in areas where blood cells are most likely to be subjected to stress and deformation. Flow through the cavities 25 in an upstream direction, is enhanced by the flushing through the ear passageways 76, 77, 78, 79 in each cavity as can be seen from FIGS. 5 and 12. The ear passageways through the ears tend to concentrate backflow in central regions of the pivot arrangements close to the pivot axes, where such cleansing flow serves to positively guard against the occurrence of clotting at low maximum pressure drops over the closed valve leaflets as occurring in heart valve prostheses implanted in the right ventricle. Because the maximum pressure drop over the closed heart valve in the right ventricle is relatively low, regurgitant flow rates or velocities through the ear passageways of the closed heart valve are not excessively high. Turbulence and shear stress caused by high local flow velocities are associated to increased risk of thrombosis formation and damage to blood cells.

If, as in the present example, the dimensioning of the ears and the cavities also leaves a pathway for backflow laterally past the edges of the leaflet ears, such backflow around and past the ears 41, 41' is to some extent entrained by the flushing through the passageways 76, 77, 78, 79. The average clearance between the edges of the ears 41 and the walls of the cavities 25 is preferably at least about 50 microns or about 0.002 inch, with the clearance being the least at the region of the apex of the curved upstream edge surface 43. There may be slightly greater clearance adjacent to the edge surfaces 45 of the ears because of the translating design of the leaflets.

The first embodiment 41 of the leaflet ears differs from the second embodiment in that the ear passageways have an open side facing an associated one of the cavities 25. This is advantageous for providing a particularly effective flushing around the outside of in particular central portions of the ears 41. An advantage of circumferentially closed passageways 78, 79 in the ears 41' is that the positioning of the ear passageways 78, 79 can be selected more freely without interfering with the camming effect of the ears along edges of the cavities 25.

While only one ear passageway may be provided in each ear, in the present example, each ear 41, 41' bounds two ear passageways 76, 77, 78, 79. By providing two or more ear passageways through each ear, a relatively large and evenly distributed flushing of the cavities 25 is obtained, while the passageways 76, 77, 78, 79 have no or relatively little effect on the camming action between the edges of the cavities and the ears. In the first embodiment, one of the passageways 76 is oriented obliquely through the leaflet ear 41, so that it extends from one of the lobes 57 to the other one of the lobes 59 and edges of the passageway 76 do not contact the convex camming surfaces 63, 65 bounding the throat, i.e. the convex camming surfaces bounding the throat do not pass over edges of the passageway 76 when the leaflet moves from the closed position to the open position or back. Thus, a particularly effective flushing of the cavities 25 is achieved with no interference with the camming action between the camming surfaces 63, 65 and the ears 41.

The single or multiple ear passageways in each ear may for instance have a width of at least 0.2 mm and more preferably at least 0.4 mm and at most 0.8 mm and more preferably 0.6 mm and a length that is for instance equal to the width or up to 3, 4, 5, 6, 7 or 8 times the width. Thus, at the low maximum pressure drops occurring over the closed valve leaflets in the right ventricle, sufficient flow for flushing without too much or too fast regurgitant flow is obtained.

In the shown embodiments, of each pair of ear passageways of an ear, a first one of the ear passageways 76, 77, 78, 79 is located at least partially in a first one of the lobes 57 and the other one is located at least partially in a second one of the lobes 59 when the leaflets 15 are in the closed positions. Thus, the flushing is concentrated in the lobes 57, 59 of the cavities 25, so that the cavities are flushed particularly effectively, even at low maximum pressure drops over the closed leaflets.

A central portion of each ear 41, 41' projects into an associated one of the cavities 25 between the ear passageways 76, 77, 78, 79 of that ear 41, 41', so that the central portions of the ears are available for suspending the leaflet relative to the cavity.

Each ear 41, 41' extends into an associated one of the cavities 25 over a depth, a central portion of each ear 41, 41' extending into the associated one of the cavities over that depth. Thus, the central portions of the ears, where relative motion between the ears and the cavities is smallest, project furthest into the cavities, thus reducing the risk of damaging blood cells between mutually shifting surfaces.

Furthermore, the central portion of each ear 41, 41' is in the throat section of the associated cavity when the leaflets are in the closed positions, so that the central portions are available for the camming action relative to the fulcrums 63, 65 bounding the throat section at least when the leaflets are moving near the closed positions.

The passageways 76, 77, 78, 79 extend into leaflet portions adjacent to the ears 41, 41'. This is advantageous for achieving a substantial flow rate into and along the cavities 25 at low maximum pressure drops over the closed leaflets.

When blood flow again reverses, as for example when the pumping stroke of the associated chamber begins again, downstream displacement, i.e. translation, of the leaflets 15 initially occurs as a result of the force of the blood against the inflow surfaces 31. As is evident from FIG. 12, the outflow surfaces of the ears 41 will quickly come in contact with the inward fulcrums 65, causing opening pivoting motion to quickly begin with the major arcuate edge surface 35 swinging downstream. The downstream edge surfaces 45 of the ears will likely reach the lower arcuate ends 75 of the downstream lobes 59 prior to the ears rotating completely about their pivot points on the fulcrums 65 until the substantially parallel position shown in FIG. 2 is reached, with the ears abutting the flat wall section 71 in each downstream lobe.

Figure 13:
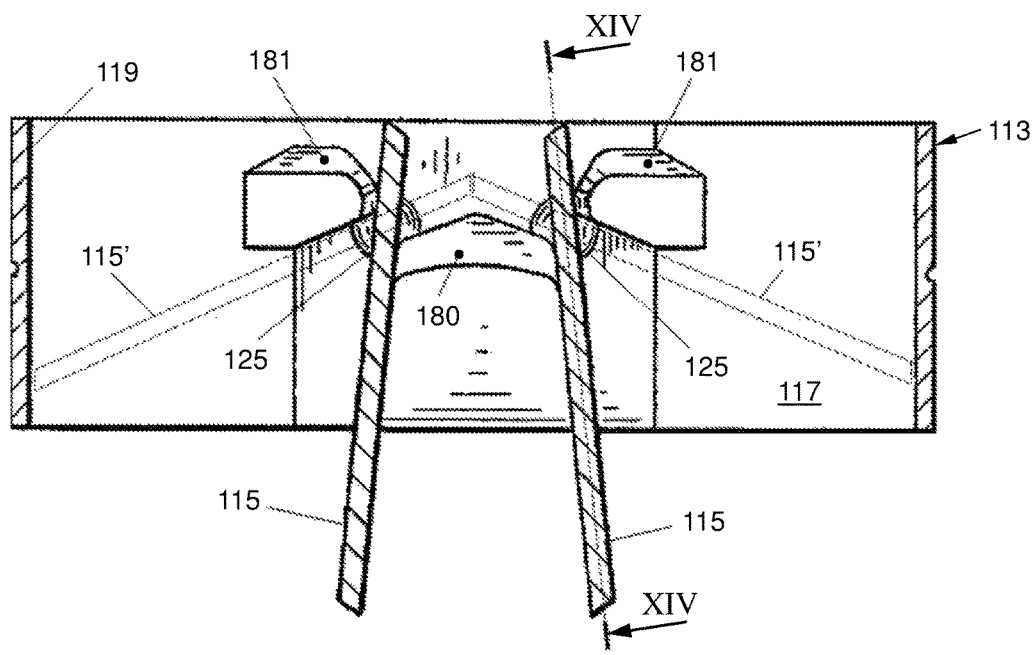
FIG. 13 is a cross-sectional side view of another example of a valve according to the invention.
Figure 14:
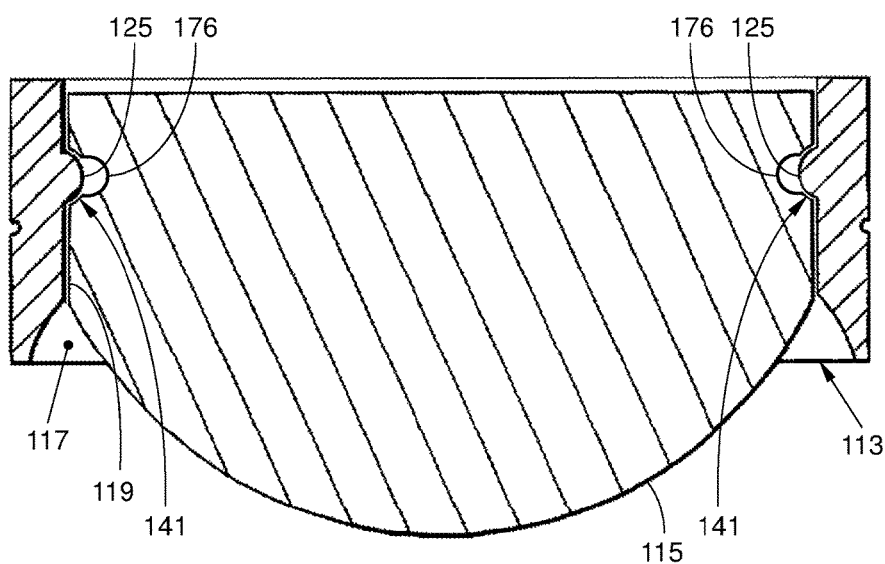
FIG. 14 is a cross-sectional view along line XIV-XIV in FIG. 13.

FIGS. 13 and 14 show another example of an application of the principle that the pivot arrangement of a heart valve is flushed effectively in its most thrombogenic areas closely around the pivot axes of the leaflet, where movements of the leaflet between open and closed positions are smallest, by regurgigant flow through leaflet passageways in that area, in particular at low pressure drops over the closed valve as occurring when a heart valve has been implanted in the right ventricle. The valve according to this example is based on a valve disclosed in U.S. Pat. No. 5,354,330.

As is best seen in FIG. 13, the valve according to this example has a generally annular valve body 113 having an interior wall surface 119 which defines a valve body passageway 117 for blood flow there through which is generally symmetrical about a longitudinal centerline. A pair of cooperating leaflets 115 is mounted in the valve body 113 to alternate between an open position 115 (FIGS. 13 and 14) where the flow of blood in a downstream direction is permitted and a closed position (FIG. 13 dash and dot lines 115') where flow of blood in the reverse direction is substantially prevented. The pivot member sets each have a recess 141 in the side edge of the leaflet 115 and a knob 125 of the interior surface 119 of the valve body 113. Each knob 125 projects into one of the recesses 141. Furthermore, abutments 180, 181 are provided for stopping the leaflets 115 in the open and closed positions.

The recesses 141 each also bound a leaflet passageway 176 through the recess 141. The leaflet passageways 176 each form a leaflet passageway portion of the recess 141 leaving a distance to the interior surface 119 of the valve body 113, which is larger than a clearance between the interior surface 119 of the valve body and portions of the side edge of the leaflet 115 adjacent to the passageway. This allows flow through that recess 141 when the leaflets 115 are in the closed positions 115'. The leaflet passageways of this embodiment ensure that regurgitant flow is concentrated along central portions of the knob 125 and the recesses 141 around the pivoting axes of the leaflets 115. Thus, the valve is most effectively flushed in an area around the most stationary zones of the leaflets 115 where risk of formation of a thrombosis is highest.

For ensuring that a regurgitant flow of sufficient magnitude is obtained, the leaflet passageways preferably each have an overall width in a direction perpendicular to a nearest portion of said surface of said valve body, that is larger than twice and preferably larger than, in order of increasing preference, three, five or ten times the clearance between the interior surface 119 of the valve body 113 and portions of the side edge of the leaflet 115 adjacent to the leaflet passageway 176.

For concentrating the regurgitant flow in the central areas around the pivot axes and leaving large bearing surfaces against the knobs 125, the leaflet passageways 176 are each located spaced from the ends of that recess 141 that are upstream and downstream when the leaflet 115 is in its open position. Also for this purpose, the leaflet passageways 176 each have a width, measured in a tangential direction of the interior wall surface 119, that is at least 20% and more preferably 30% smaller than a distance from the upstream end to the downstream end of that recess 141.

To ensure sufficient regurgitant flow for significantly reducing the formation of thromboses where the leaflets are hinged to the valve body and in particular in the area of the hinge axis, the cross-sectional surface area of the passages bounded by each of the ears or recesses is preferably at least 0.2 mm$^2$ per ear or recess and more preferably at least 0.4 mm$^2$, 0.6 mm$^2$ or 0.7 mm$^2$ per ear or recess. On the other hand, to avoid more regurgitant flow than is useful for counteracting the formation of thromboses where the leaflets are hinged to the valve body and in particular in the area of the hinge axis, the cross-sectional surface area of the passages bounded by each of the ears or recesses is preferably at most 2.5 mm$^2$ per ear or recess and more preferably at most 1.5 mm$^2$, 1.0 mm$^2$ or 0.9 mm$^2$ per ear or recess.

Although the invention has been described with respect to certain preferred embodiments, which include what the inventors presently consider to be the best mode for carrying out the invention, it should be understood that various changes and modifications that would be obvious to one having the ordinary skill in this art may be made without departing from the scope of the invention which is defined by the claims appended hereto. For example, the invention can also be embodied in a valve of a different basic design. More in particular, as indicated, the invention is not limited to occluders in the form of leaflets having flat body sections but is considered to be also applicable to leaflets having curved body sections with substantially rectilinear surfaces. Also, the number of passageways bounded by each ear or recess may be larger or smaller. For instance, a single passageway may extend obliquely through each ear from a first one of the lobes of the associated cavity to the other lobe of the associated cavity, the ends of the passageway being positioned such that, regardless the operational position of the leaflet, none of the edges of the passageway contacts the convex fulcrums bounding the throat area between these lobes. Thus, a particularly effective flushing through the throat area of the cavity between the lobes is obtained without interfering with the camming action between the leaflet and the convex fulcrums bounding the throat area. Also, each recesses may bound for instance two or three passageways.

Several features have been described as part of the same or separate embodiments. However, it will be appreciated that the scope of the invention also includes embodiments having combinations of all or some of these features other than the specific combinations of features embodied in the examples.

The invention claimed is:

1. A prosthetic heart valve including
a generally annular valve body having an interior, generally arcuate wall surface which defines a valve body passageway for blood flow therethrough which is generally symmetrical about a longitudinal centerline,
a pair of cooperating leaflets, said leaflets being mounted in said valve body to alternate between an open position where the flow of blood in a downstream direction is permitted and a closed position where the flow of blood in the reverse direction is counteracted, and
a pivot arrangement with pivot member sets on diametrically opposite sides of each leaflet, which guides said leaflets in moving between said open and closed positions,
said pivot member sets each comprising a recess in the side edge of said leaflet and a knob of said interior surface of said valve body, said knob projecting into said recess,
each of said recesses having opposite ends, the ends of each recess being located upstream and downstream of that recess when said leaflets are in the open position, and
each of said recesses bounding at least one leaflet passageway through that recess from an inflow side of said leaflet to an outflow side of said leaflet,
said at least one leaflet passageway forming a leaflet passageway portion of said recess at a distance to said interior surface of said valve body, which is larger than a clearance between said interior surface of said valve body and portions of said side edge of said leaflet adjacent to said leaflet passageway, for allowing regurgitant flow through that recess in response to a pressure drop over said leaflet when said leaflets are in said closed positions.

2. A heart valve according to claim 1, wherein each recess bounds at least one further leaflet passageway.

3. A heart valve according to claim 2, wherein a central portion of each ear projects into an associated one of said cavities between said at least two of said leaflet passageways.

4. A heart valve according to claim 3, wherein said cavities each have an upstream lobe and a downstream lobe which are separated by a throat section defined by convex outward and inward fulcrums and wherein said central portion of each ear is in said throat section when said leaflets are in said closed positions.

5. A heart valve according to claim 4, wherein at least one of the passageways is oriented obliquely through the leaflet, so that it extends from one of the lobes to the other one of the lobes of the associated cavity and edges of said at least one of the passageways do not contact any of the convex outward and inward fulcrums defining the throat in any operational position of the leaflet.

6. A heart valve according to claim 1, wherein said leaflet passageways each have an overall width in a direction perpendicular to a nearest portion of said surface of said valve body, that is larger than twice said clearance between said interior surface of said valve body and portions of said side edge of said leaflet adjacent to said passageway.

7. A heart valve according to claim 1, wherein said leaflets have substantially rectilinear outflow surfaces facing downstream when the leaflets are closed and inflow surfaces facing upstream when said leaflets are closed,
wherein said inflow surface and said outflow surface of each leaflet are flat and parallel to each other, and
wherein said at least one leaflet passageway is located spaced from said upstream and downstream ends of that recess.

8. A heart valve according to claim 7, wherein said leaflet passageways each have a width measured in a tangential direction of said interior wall surface, that is at least 20% smaller than a distance from said upstream end to said downstream end of said recess.

9. A heart valve according to claim 1, wherein the passages bounded by each of the recesses have a cross-sectional surface area of at least 0.2 mm$^2$ per recess.

10. A heart valve according to claim 1, wherein the passages bounded by each of the recesses have a cross-sectional surface area of at most 2.5 mm$^2$ per recess.

11. A prosthetic heart valve including
a generally annular valve body having an interior, generally arcuate wall surface which defines a valve body passageway for blood flow therethrough which is generally symmetrical about a longitudinal centerline,
a pair of cooperating leaflets, said leaflets being mounted in said valve body to alternate between an open position where the flow of blood in a downstream direction is permitted and a closed position where the flow of blood in the reverse direction is counteracted, and
a pivot arrangement which guides said leaflets in moving between said open and closed positions,
said pivot arrangement comprising ears respectively projecting laterally from opposite side edges of each of said leaflets and two pairs of diametrically opposed cavities in said interior surface of said valve body, each of said ears projecting from said side edges into an associated one of said cavities,
said ears each having opposite ends, the ends of each ear being located upstream and downstream of that ear when said leaflets are in the open position, and
each of said ears bounding at least one leaflet passageway through that ear from an inflow side of said leaflet to an outflow side of said leaflet,
said at least one leaflet passageway being located spaced from said upstream and downstream ends of that ear for allowing regurgitant flow through that ear and the associated one of said cavities in response to a pressure drop over said leaflet when said leaflets are in said closed positions.

12. A heart valve according to claim 11, wherein said at least one leaflet passageway an open side facing an associated one of said cavities.

13. A heart valve according to claim 11, wherein each ear bounds at least one further leaflet passageway.

14. A heart valve according to claim 13, wherein said cavities each have an upstream lobe and a downstream lobe which are separated by a throat section defined by convex outward and inward fulcrums, and wherein a first one of said at least two of said leaflet passageways is located at least partially in a first one of said lobes and a second one of said at least two of said leaflet passageways is located at least partially in a second one of said lobes when said leaflets are in said closed positions.

15. A heart valve according to claim 11, wherein each ear extends into an associated one of said cavities over a depth, a central portion of each ear extending into the associated one of said cavities over said depth.

16. A heart valve according to claim 11, wherein said at least one passageway extends into a leaf portion adjacent to said ear.

17. A heart valve according to claim 11, wherein said leaflets have substantially rectilinear outflow surfaces facing downstream when the leaflets are closed and inflow surfaces facing upstream when said leaflets are closed, wherein said inflow surface and said outflow surface of each leaflet are flat and parallel to each other.

18. A heart valve according to claim 17, wherein said leaflet ears have inflow and outflow surfaces which are substantially coplanar with said inflow and outflow surfaces of said leaflets.

19. A heart valve according to claim 11, wherein said leaflet passageways each have an overall width in a direction perpendicular to a nearest portion of said surface of said valve body, that is larger than twice said clearance between said interior surface of said valve body and portions of said side edge of said leaflet adjacent to said passageway.

20. A heart valve according to claim 11, wherein the passages bounded by each of the ears have a cross-sectional surface area of at least 0.2 mm$^2$ per ear.

21. A heart valve according to claim 11, wherein the passages bounded by each of the ears have a cross-sectional surface area of at most 2.5 mm$^2$ per ear.

* * * * *